United States Patent [19]
Ito et al.

[11] Patent Number: 5,734,472
[45] Date of Patent: Mar. 31, 1998

[54] METHOD AND APPRATUS FOR MEASURING THICKNESS OF BIREFRINGENCE LAYER

[75] Inventors: Masami Ito, Moriguchi; Kanji Nishii, Osaka; Kenji Takamoto, Neyagawa; Atsushi Fukui, Osaka, all of Japan

[73] Assignee: Matsushita Electric Industrial Co., Ltd., Osaka-fu, Japan

[21] Appl. No.: 668,136

[22] Filed: Jun. 21, 1996

[30] Foreign Application Priority Data

Jun. 26, 1995 [JP] Japan .................................. 7-158967

[51] Int. Cl.$^6$ ................................................ G01N 21/21
[52] U.S. Cl. ........................... 356/364; 356/365; 356/367
[58] Field of Search ................................ 356/364, 365, 356/366, 367, 368, 369, 382, 33, 34, 35; 250/225

[56] References Cited

U.S. PATENT DOCUMENTS

| | | | |
|---|---|---|---|
| 4,684,256 | 8/1987 | Tsumura et al. | 356/367 |
| 5,239,365 | 8/1993 | Inoue | 356/367 |
| 5,311,284 | 5/1994 | Nishino | 356/364 |
| 5,406,371 | 4/1995 | Sakai et al. | 356/367 |
| 5,434,671 | 7/1995 | Sumiyoshi et al. | 356/367 |
| 5,471,306 | 11/1995 | Yui et al. | 356/367 |
| 5,504,581 | 4/1996 | Nagata et al. | 356/364 |
| 5,532,823 | 7/1996 | Fukui et al. | 356/364 |

FOREIGN PATENT DOCUMENTS

3-269305  11/1991  Japan .

*Primary Examiner*—Frank G. Font
*Assistant Examiner*—Michael P. Stafira
*Attorney, Agent, or Firm*—Wenderoth, Lind & Ponack

[57] ABSTRACT

A liquid crystal layer is interposed between two polarizers arranged in a parallel Nicol or crossed Nicol manner, and a phase plate is set between two polarizers so that the transmission direction of the first polarizer coincides with the optical axis. Then, a rotation angle at which optical intensity transmitted through the second polarizer has an extreme value to be determined, and the thickness of the birefringence layer is calculated according to the rotation angle of the phase plate. In a different method, a half-wave plate is used. First, the liquid crystal layer is set at a position where an optical intensity of the transmission light has an extreme value, and the half-wave plate provided between the two polarizers is set so that a transmission direction of the first polarizer coincides with the optical axis. Then, a rotation angle of the phase plate is determined at which an optical intensity of light transmitted through the second polarizer has an extreme value. Then, the thickness is calculated according to the rotation angle of the half-wave plate. Thus, the thickness is measured in a short time even for a liquid crystal that does not have a twist angle of 90° or in which the rubbing direction is not known.

10 Claims, 9 Drawing Sheets

Angle of rotation α of phase plate

Angle of rotation α of phase plate

Angle of rotation α of phase plate

Angle of rotation α of phase plate

METHOD AND APPRATUS FOR MEASURING THICKNESS OF BIREFRINGENCE LAYER

BACKGROUND OF THE INVENTION

1. Field of the Invention

The present invention relates to a method and apparatus for measuring a thickness of a birefringence layer of an object such as a liquid crystal.

2. Description of the Prior Art

In a prior art apparatus for measuring a thickness of a liquid crystal layer, a liquid crystal cell to be measured is placed between a polarizer and an analyzer. A light source generates a light having a plurality of wavelengths, and a monochromator or a spectrometer receives the light and generates a light having a single wavelength $\lambda$. The light is passed through the polarizer, the liquid crystal layer and the analyzer successively, and the light transmitting through the analyzer is detected by a photosensor. The direction of the transmission axis of the polarizer is parallel to the rubbing direction of the incident side of the liquid crystal cell. The liquid crystal which is measured has a liquid crystal twist angle of about 90°.

The thickness of a liquid crystal layer is conventionally measured with the apparatus described above. If the wavelength of a light emitted by the monochromator is represented as $\lambda$, the transmittance $T$ of the light transmitted through the polarizer, the liquid crystal and the analyzer is expressed as follows:

$$T = \sin^2(\pi/2) \sqrt{1+u^2} \ /(1+u^2), \quad (1)$$

where $$u = 2\Delta n d/\lambda,$$

$\Delta n$ denotes the degree of birefringence of a liquid crystal or the difference between a normal index of refraction and an abnormal index of refraction, and $d$ denotes a thickness of the liquid crystal layer. Then, Eq. (2) is derived from Eq. (1) if the wavelength at which the transmittance $T$ becomes zero is denoted as $\lambda_s$.

$$d = \lambda_s/\Delta n \times \sqrt{m^2 - 1/4}, \quad (2)$$

where $$m=1, 2, 3, \ldots$$

Thus, the wavelength $\lambda_s$ at which the optical intensity detected by the photosensor becomes zero, or the wavelength $\lambda_s$ at which the transmittance $T$ becomes zero is determined by changing the wavelength of the monochromator. The wavelength $\lambda_s$ is substituted in Eq. (2) in order to determine the thickness $d$ of the liquid crystal layer.

However, the method explained above has several disadvantages. First, a liquid crystal layer of which the thickness can be measured is limited to a layer having a twist angle of about 90°. Further, the rubbing direction of the liquid crystal cell must be the same as the transmission direction of the two polarizers, thus the rubbing direction has to be determined. However, it is usually difficult to measure the rubbing direction, and it is impossible to set the rubbing direction of the liquid crystal correctly to agree with the transmission direction of the two polarizers. Further, a monochromatic meter or a spectrometer which is needed, requires about one minute of time for the measurement. Therefore, the conventional method cannot be applied to uses such as in-line inspections that require high speed processing. Finally, because a monochromatic meter or a spectrometer is used, the conventional apparatus has a complicated structure and a high cost.

SUMMARY OF THE INVENTION

An object of the present invention is to provide a method and an apparatus for measuring a thickness of a birefringence layer with improved precision and at a high speed to enable in-line inspections. A further object is to provide the above advantage even for a liquid crystal that does not have a twist angle of 90° or on which the rubbing direction is not known, and to allow the apparatus to be fabricated at a low cost.

In one aspect of the invention, the thickness of a birefringence layer is measured as follows: an object to be measured having a birefringence layer such as a liquid crystal cell and a phase plate are provided in an optical path of a light between first and second polarizers in a parallel Nicol or crossed Nicol arrangement. The phase plate is set so that a direction of transmission of the first polarizer coincides with an optical axis of the light. Then, the phase plate is rotated while detecting an optical intensity of light transmitted through the second polarizer. A rotation angle of the phase plate is determined at which the optical intensity has an extreme value. Then, the thickness of the birefringence layer is calculated according to the rotation angle at the extreme value.

In a second aspect of the invention, the thickness of a birefringence layer having an orientation direction, such as a liquid crystal having rubbing direction, is measured in a different way as follows: in this method, a $\lambda/2$ plate (half-wave plate) is used as the phase plate, and the object to be measured having a birefringence layer is set so as to be rotated. First, the object to be measured is rotated, and it is set at a position so that an optical intensity of light transmitted through the second polarizer has an extreme value. Next, the $\lambda/2$ plate is rotated, and a rotation angle of the $\lambda/2$ plate is determined at which an optical intensity of light transmitted to the second polarizer has an extreme value. Then, a thickness of the birefringence layer is calculated according to the rotation angle of the $\lambda/2$ plate.

An advantage of the present invention is that the thickness is measured at a high rate of speed.

Another advantage of the present invention is that a liquid crystal cell having a twist angle other than 90° can be measured.

A further advantage of the present invention is that the thickness can be measured with a very simple optical system which is inexpensive to fabricate.

BRIEF DESCRIPTION OF THE DRAWINGS

These and other objects and features of the present invention will become clear from the following description taken in conjunction with the preferred embodiments thereof with reference to the accompanying drawings, in which.

DETAILED DESCRIPTION OF THE PREFERRED EMBODIMENTS

Figure 1:
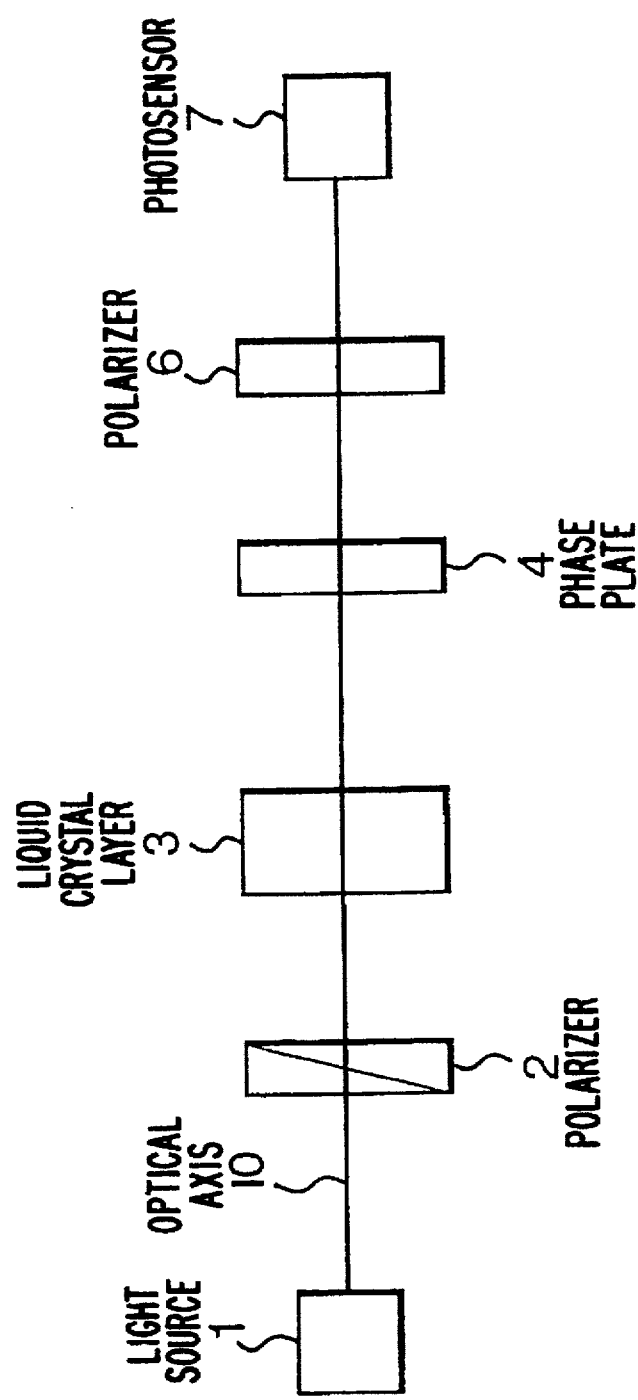
FIG. 1 is a diagram of a basic optical system for a method for measuring a thickness of birefringence layer of a first embodiment of the invention.

Referring now to the drawings, wherein like reference characters designate like or corresponding parts throughout the several views, FIG. 1 shows a basic optical system for measuring a thickness of a birefringence layer of a first embodiment of the invention. In FIG. 1, a single wavelength light source 1 such as a laser device emits a light of a wavelength λ. Along the optical axis 10 of the light, a polarizer 2, a liquid crystal layer 3 contained in a liquid crystal cell, a phase plate 4, another polarizer 6 and a photosensor 7 are arranged successively. The liquid crystal layer 3 is an example of an object to be measured having a birefringence layer, and it has ordinary index $n_o$ and extraordinary index $n_e$. The object 3 is provided between the two polarizers 2 and 6 that are set in a parallel Nicol or a crossed Nicol arrangement. The phase plate 4 having a phase difference δ is provided between the two polarizers 2, 6. Thus, the photosensor 7 detects a light transmitted through the second polarizer 6.

Figure 2:
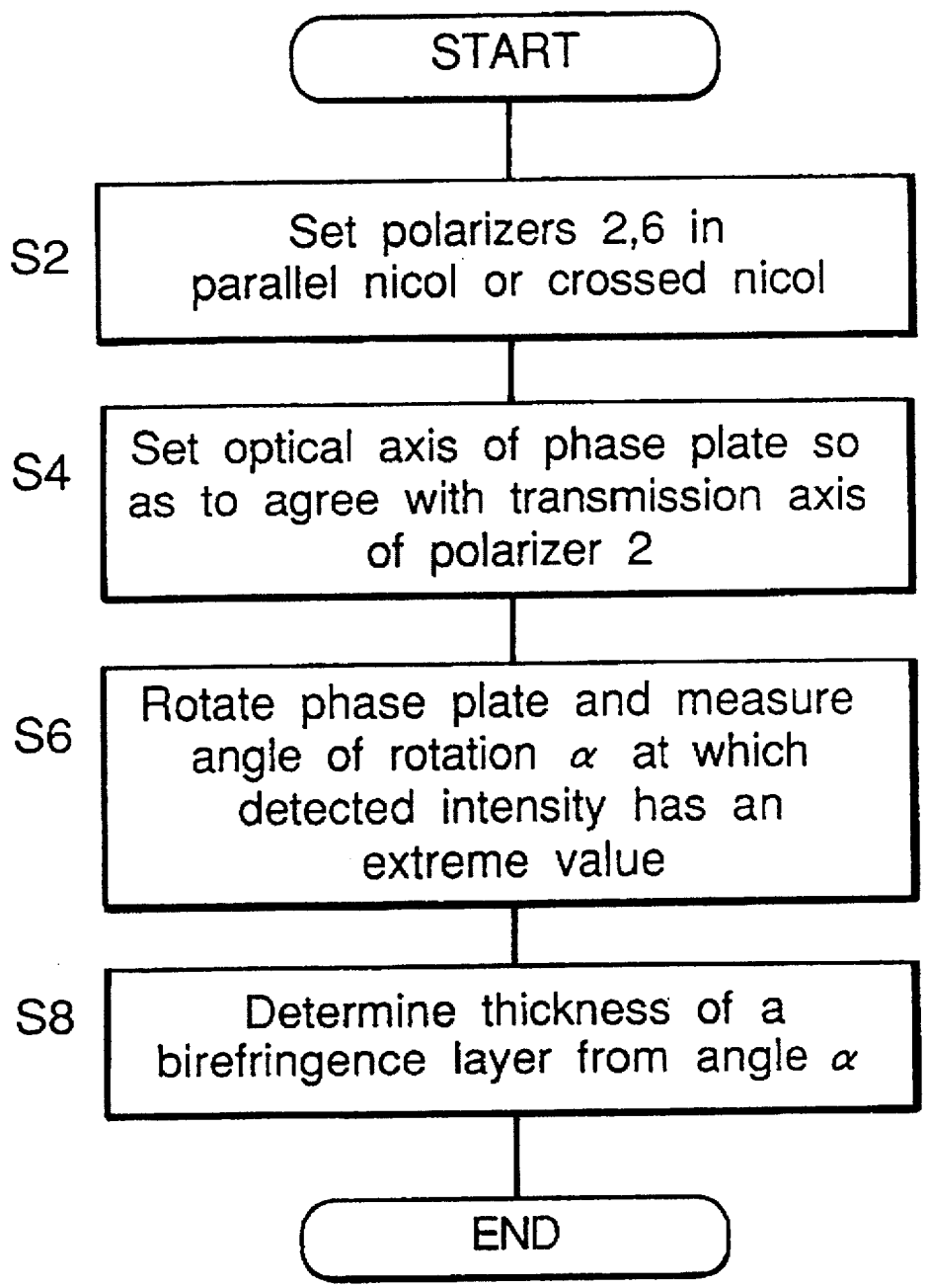
FIG. 2 is a flow chart of the measuring method of the first embodiment.

Next, with reference to the flowchart of FIG. 2, the measurement of a thickness of the birefringence layer 3 with use of the optical system having the above-mentioned structure is explained. First, the first polarizer 2 and the second polarizer 6 are set in a parallel Nicol or a crossed Nicol arrangement with a liquid crystal layer 3 interposed between them (step S2). Next, the optical axis of the phase plate 4 is set to coincide with the transmission axis of the first polarizer 2 (step S4). Then, the phase plate 4 is rotated, and a rotation angle α at which the detection intensity of the photosensor 7 has an extreme value is measured (step S6). Then, the rotation angle α measured is substituted into Eq. (11) explained later, and the thickness of the birefringence layer (liquid crystal layer) 3 is calculated (step S8).

Next, the principle of the above-mentioned method for measuring the thickness of a birefringence layer (liquid crystal layer) is explained with reference to numerical formulas.

Figure 3:
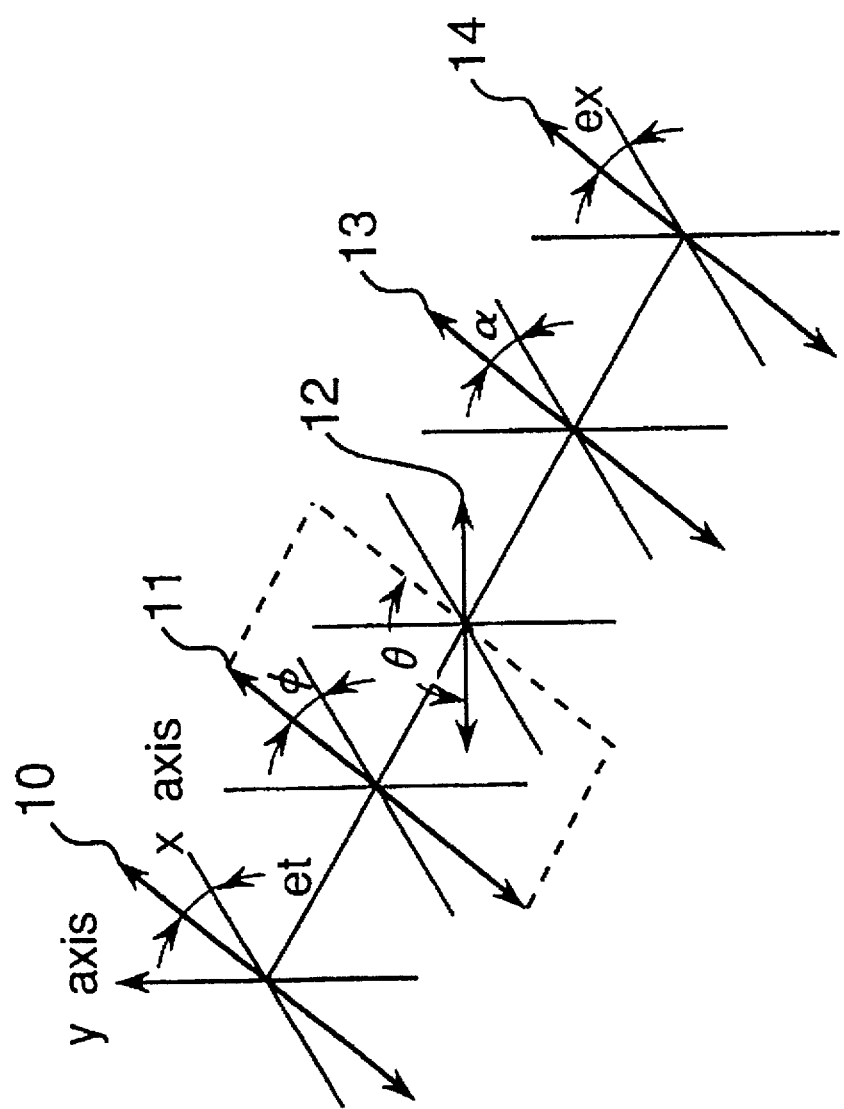
FIG. 3 is a diagram for explaining coordinates in the optical system of the embodiment.

FIG. 3 shows coordinates of the optical system shown in FIG. 1. In FIG. 3, reference numeral 10 denotes the transmission axis of the polarizer 2, and an angle relative to x axis is denoted as $e_t$. Reference numeral 11 denotes a rubbing direction at the incoming side of the liquid crystal 3, and an angle relative to x axis is taken as φ. Reference numeral 12 denotes the rubbing direction of the liquid crystal cell at the outgoing side, and at twist angle defined as an angle between the rubbing directions at the incoming side of the cell and at the outgoing side is taken as θ. The rubbing direction represents a direction of the liquid crystal orientation in the liquid crystal cell. Reference numeral 13 denotes the optical axis of the phase plate 4, and an angle relative to x axis is taken as α. Reference numeral 14 denotes the transmission axis of the polarizer 6, and an angle relative to x axis is taken as $e_x$.

By using the coordinates stated above, a light transmitted through the polarizer 2 is described by Eq. (3) by using a Jones vector A.

$$A = \begin{pmatrix} \cos(e_t) \\ \sin(e_t) \end{pmatrix}. \tag{3}$$

Further, Jones matrix B of the liquid crystal 3 is shown in Eq. (4), Jones matrix C of the phase plate 4 is shown in Eq. (5), and Jones matrix D of the other polarizer 6 is shown in Eq. (6).

$$B = \exp(-i\eta) \begin{pmatrix} p+qi & r+si \\ -r+si & p-qi \end{pmatrix}, \tag{4}$$

where $p = \cos(\gamma)\cos(\theta) + (\theta/\gamma)\sin(\gamma)\sin(\theta)$, $q = -(\beta/\gamma)\sin(\gamma)\cos(\theta + 2\phi)$, $r = -\cos(\gamma)\sin(\theta) + (\theta/\gamma)\sin(\gamma)\cos(\theta)$, $s = -(\beta/\gamma)\sin(\gamma)\sin(\theta + 2\phi)$, $\gamma = \sqrt{\beta^2 + \theta^2}$, $\eta = d(n_e + n_o)\pi/\lambda$, and $\beta = d(n_e - n_o)\pi/\lambda$.

$$C = R(\alpha) \begin{pmatrix} \exp(i\delta/2) & 0 \\ 0 & \exp(-i\delta/2) \end{pmatrix}, \tag{5}$$

where $$R(\theta) = \begin{pmatrix} \cos\theta & -\sin\theta \\ \sin\theta & \cos\theta \end{pmatrix}.$$

$$D = R(e_x) \begin{pmatrix} 1 & 0 \\ 0 & 0 \end{pmatrix} R(-e_x). \tag{6}$$

Therefore, Jones vector $E(E_x, E_y)$ of light transmitted through the polarizer 6 is shown in Eq. (7), and the intensity F detected by the photosensor 7 is shown in Eq. (8).

$$E = \begin{pmatrix} E_x \\ E_y \end{pmatrix} = DCBA. \quad (7)$$

$$F = |E_x|^2 + |E_y|^2. \quad (8)$$

Generality is not lost if the direction of the transmission axis of the polarizer 2 is taken as $e_i=0$. Then, $e_i$ is set as zero. Then, the direction of the transmission axis $e_x$ of the other polarizer 6 is set to have $e_x=0°$ for a parallel Nicol arrangement or 90° for a crossed Nicol arrangement.

For the case of a parallel Nicol arrangement, the intensity F1 detected by the photosensor 7 is shown by Eq. (9), and for the case of a crossed Nicol arrangement, the intensity F2 detected by the photosensor 7 is shown by Eq. (10).

$$F_1 = F_{ei=0,ex=0} \quad (9)$$

$$= \frac{1}{4} \{(-p^2 - q^2 + r^2 + s^2)\cos(\delta) + p^2 + q^2 - r^2 -$$

$$s^2\}\cos(4\alpha) + \frac{1}{2} \{(pr - sq)\cos(\delta) - pr + sq\}\sin(4\alpha) -$$

$$(ps + qr)\sin(\delta)\sin(2\alpha) + \frac{1}{4} \{p^2 + q^2 - r^2 - s^2\}\cos(\delta) +$$

$$\frac{3}{4} (p^2 + q^2) + \frac{1}{4} (r^2 + s^2).$$

$$F_2 = F_{ei=0,ex=\frac{\pi}{2}} \quad (10)$$

$$= \frac{1}{4} \{(p^2 + q^2 - r^2 - s^2)\cos(\delta) - p^2 - q^2 + r^2 +$$

$$s^2\}\cos(4\alpha) + \frac{1}{2} \{(-pr - sq)\cos(\delta) + pr - sq\}\sin(4\alpha) +$$

$$(qr + ps)\sin(\delta)\sin(2\alpha) + \frac{1}{4} \{-p^2 - q^2 + r^2 + s^2\}\cos(\delta) +$$

$$\frac{1}{4} (p^2 + q^2) + \frac{3}{4} (r^2 + s^2).$$

Next, simulation of the detection intensities F1 and F2 is performed with the simulation conditions compiled in Table 1.

TABLE 1

| Degree of birefringence of liquid crystal ($\Delta n = n_e - n_o$) | 0.1 |
|---|---|
| Twist angle of liquid crystal ($\theta$) | 88° |
| Rubbing direction of liquid crystal ($\phi$) | 46° |
| Thickness of liquid crystal layer (d: μm) | 5.0 |
| Measurement wavelength ($\lambda$: nm) | 633 |

Figure 4:
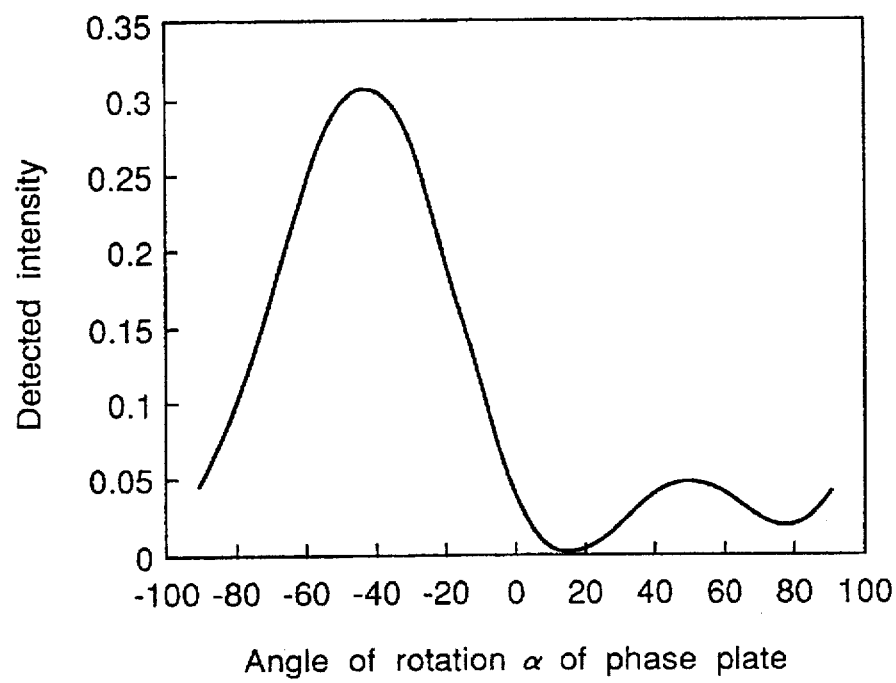
FIG. 4 is a graph of a detected intensity plotted against an angle of rotation of a phase plate in a case wherein the polarizers are in a parallel Nicol arrangement and the phase differences δ of the phase plate 4 is λ/8 where λ is a wavelength.
Figure 5:
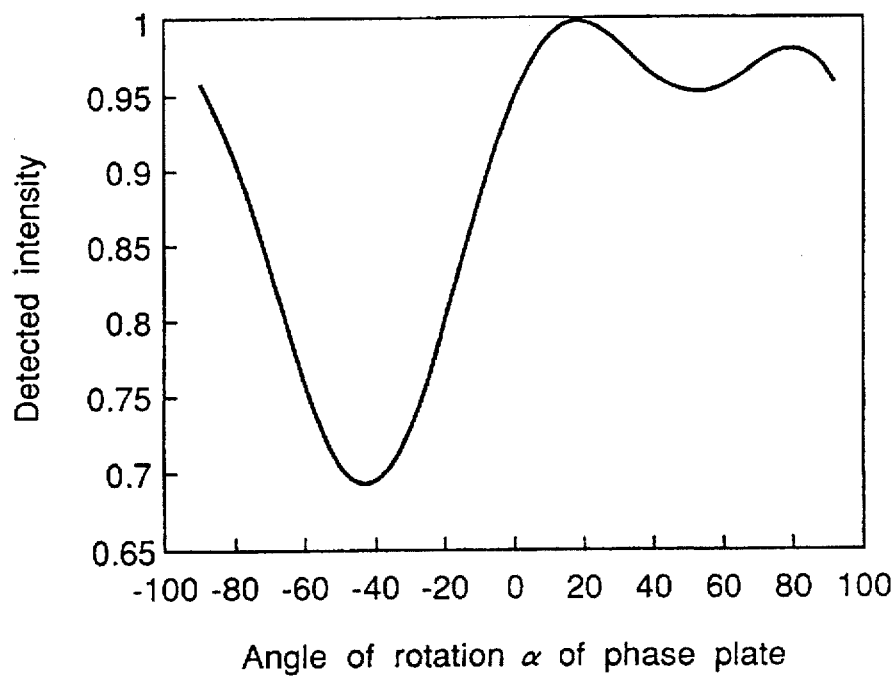
FIG. 5 is a graph of a detected intensity plotted against an angle of rotation of a phase plate in a case where the polarizers are in a crossed Nicol arrangement and the phase differences δ of the phase plate 4 is λ/8.
Figure 6:
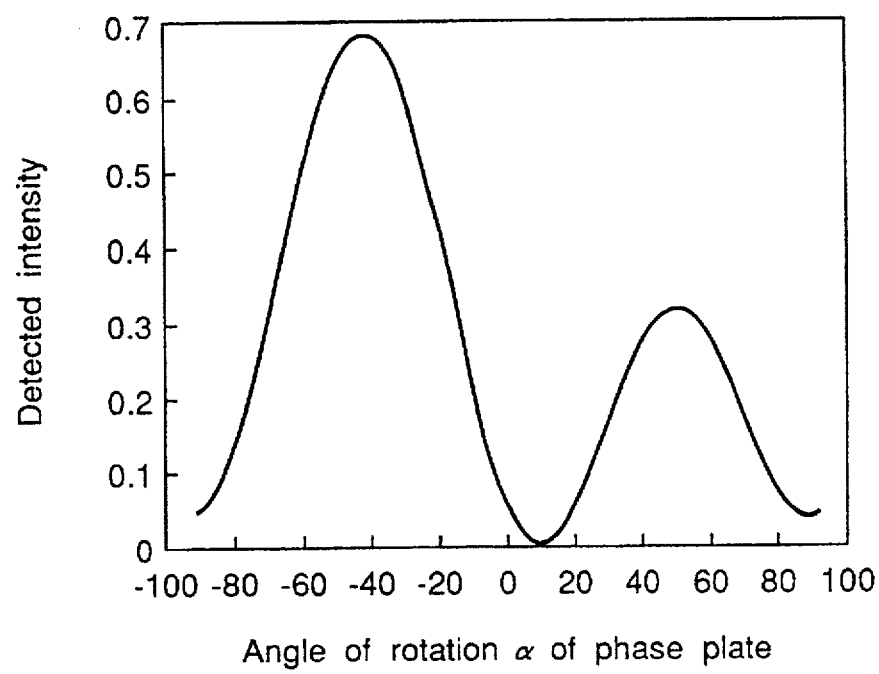
FIG. 6 is a graph of a detected intensity plotted against an angle of rotation of a phase plate in a case where the polarizers are in a parallel Nicol arrangement and the phase differences δ of the phase plate 4 is λ/4.
Figure 7:
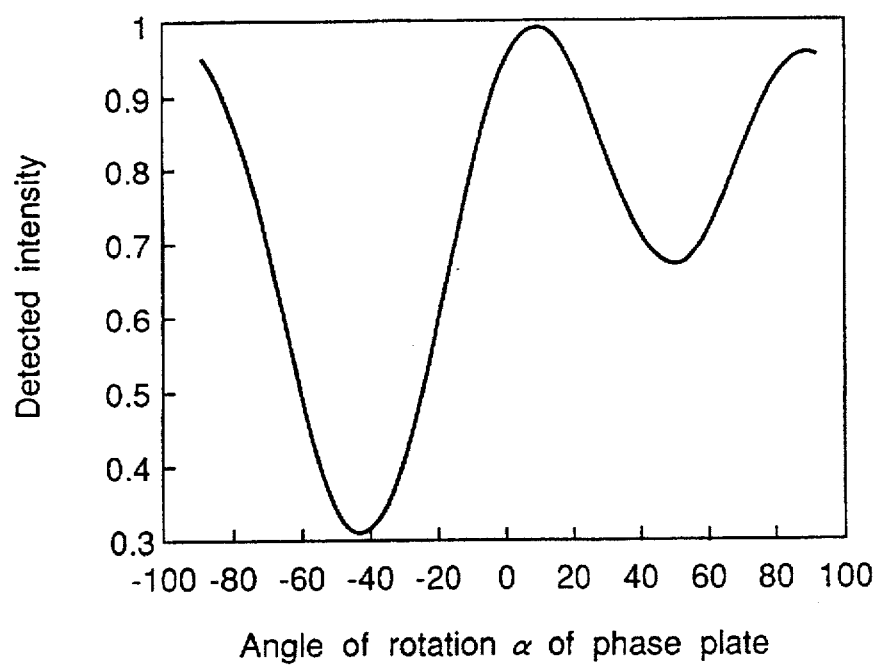
FIG. 7 is a graph of a detected intensity plotted against an angle of rotation of a phase plate in a case where the polarizers are in a crossed Nicol arrangement and the phase differences δ of the phase plate 4 is λ/4.
Figure 8:
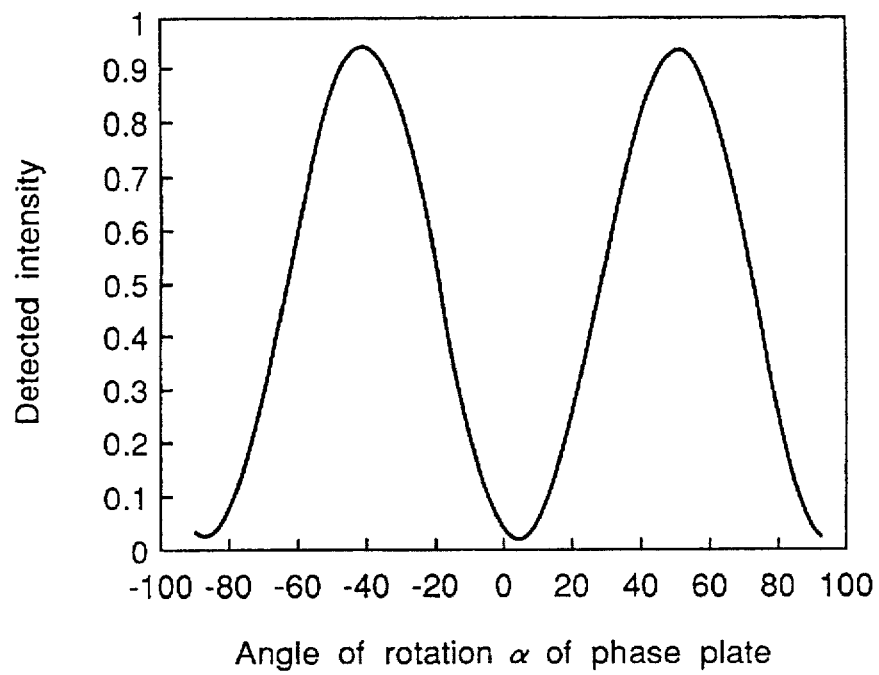
FIG. 8 is a graph of a detected intensity plotted against an angle of rotation of a phase plate in a case where the polarizers are in a parallel Nicol arrangement and the phase differences δ of the phase plate 4 is λ/2.
Figure 9:
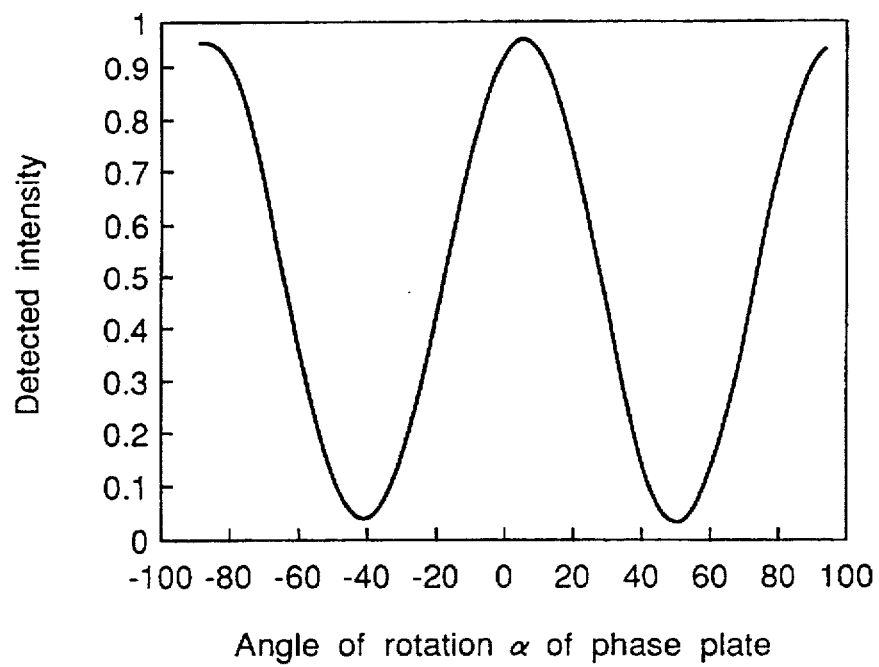
FIG. 9 is a graph of a detected intensity plotted against an angle of rotation of a phase plate in a case where the polarizers are in a crossed Nicol arrangement and the phase differences δ of the phase plate 4 is λ/2.

FIGS. 4–9 show the relationship between the intensity detected with the photosensor 7 and the rotation angle a of the phase plate 4 for a parallel Nicol arrangement or for a crossed Nicol arrangement. Table 2 shows the relation between the polarization state of the phase difference of the phase plate 4 and the polarizers 2 and 6 with the number of the drawings. In other words, FIG. 4 shows a case of the polarizers in a parallel Nicol arrangement and the phase differences δ of the phase plate 4 is λ/8; FIG. 5 shows a case of the polarizers in a crossed Nicol arrangement and the phase differences δ of the phase plate 4 is λ/8; FIG. 6 shows a case of the polarizers in a parallel Nicol arrangement and the phase differences δ of the phase plate 4 is λ/4; FIG. 7 shows a case of the polarizers in a crossed Nicol arrangement and the phase differences δ of the phase plate 4 is λ/4; FIG. 8 shows a case of the polarizers in a parallel Nicol arrangement and the phase differences δ of the phase plate is λ/2; and FIG. 9 shows a case of the polarizers in a crossed Nicol arrangement and the phase differences δ of the phase plate 4 is λ/2.

TABLE 2

| Number of drawing | Phase difference δ | Polarization condition |
|---|---|---|
| 4 | λ/8 | Parallel Nicol |
| 5 | λ/8 | Crossed Nicol |
| 6 | λ/4 | Parallel Nicol |
| 7 | λ/4 | Crossed Nicol |
| 8 | λ/2 | Parallel Nicol |
| 9 | λ/2 | Crossed Nicol |

As will be understood from FIGS. 4–9, the optical intensity detected by the photosensor 7 has an extreme value irrespective of a phase difference between the phase plate 4 and the polarization state. The rotation angle α of the phase plate 4 at an extreme value can be determined by differentiating Eqs. (9) and (10) with α, as shown in Eqs. (11) and (12).

$$\frac{\partial F_1}{\partial \alpha} = 0. \quad (11)$$

$$\therefore \{(p^2 + q^2 - r^2 - s^2)\cos(\delta) - p^2 - q^2 + r^2 + s^2\}\sin(4\alpha) +$$

$$2\{(pr - sq)\cos(\delta) - pr + sq\}\sin(4\alpha) - 2(ps + qr)\sin(\delta)\cos(2\alpha) = 0.$$

$$\frac{\partial F_2}{\partial \alpha} = 0. \quad (12)$$

$$\therefore \{(p^2 + q^2 - r^2 - s^2)\cos(\delta) - p^2 - q^2 + r^2 + s^2\}\sin(4\alpha) +$$

$$2\{(pr - sq)\cos(\delta) - pr + sq\}\sin(4\alpha) - 2(ps + qr)\sin(\delta)\cos(2\alpha) = 0.$$

By observing the two equations, it is realized that Eq. (11) is the same as Eq. (12).

If differences in the ordinary and extraordinary indices of the liquid crystal ($\Delta n = n_e - n_o$), twist angle of the liquid crystal ($\theta$), the measurement wavelength ($\lambda$), the phase difference ($\delta$) of the phase plate and the rotation angle α of the phase plate at an extreme value, are known in Eq. (11), only the thickness d of liquid crystal layer is not known. Then, the thickness d can be determined by solving Eq. (11).

The precision of the measurement of the thickness of the liquid crystal layer is determined by the measurement precision of the rotation angle α of the phase plate 3. Precisions in the thickness of 10 nm can be obtained With precision of the rotation angle of 0.05°. The measurement is completed in about one second where the phase plate 4 is rotated by several degrees. Thus, the present invention provides the advantage in that the measurement is performed at a high rate of speed.

As described above, according to the present embodiment, the intensity detected by the photosensor 7 is changed by rotating the phase plate 4. Then, a rotation angle e at which the intensity has an extreme value is measured, and the thickness d of the liquid crystal layer is determined at a high precision according to Eq. (11).

Figure 10:
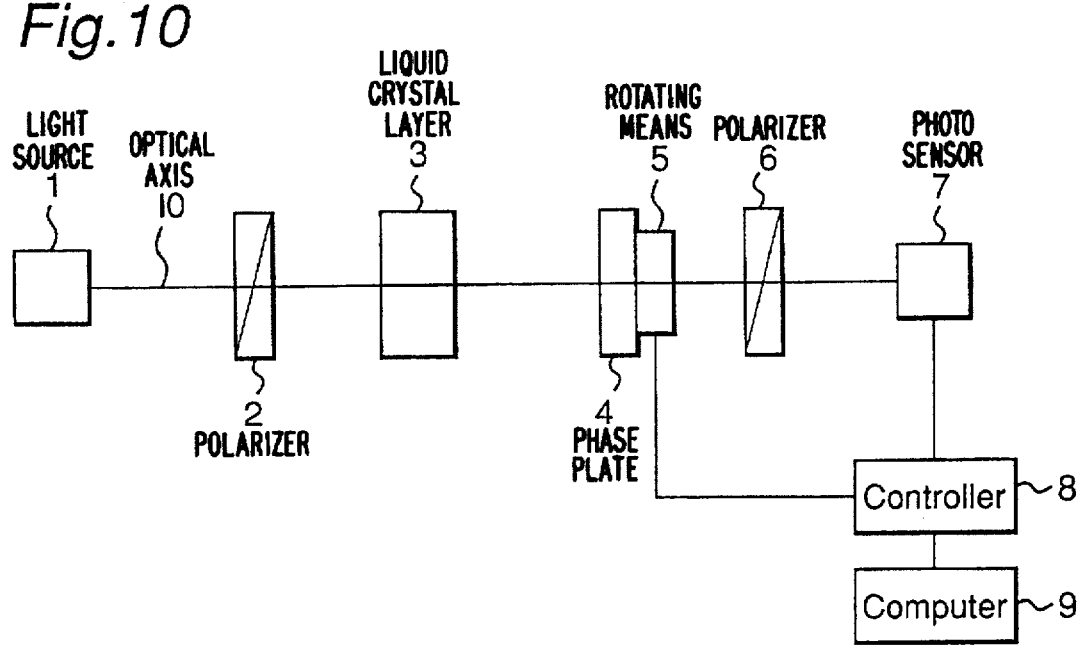
FIG. 10 is a diagram of an apparatus for measuring a thickness of birefringence layer.

FIG. 10 shows an apparatus for measuring the thickness of a birefringence layer. In FIG. 10, like reference characters denote substantially the same components shown in FIG. 1. A rotating means 5 rotates the phase plate 4. A controller 8 controls the rotating means 5 on the basis of signals from the photosensor 7, and a computer 9 calculates the thickness d of the liquid crystal 3 as an object to be measured according to the rotation angle of the phase plate 4 with the controller 8.

A method of measuring the thickness of a birefringence layer in the optical system having the above-mentioned structure is explained with reference to the flowchart of FIG.

2. The birefringence layer such as a liquid crystal cell has an orientation direction at an incidence side thereof. First, the polarizers 2 and 6 are set in a parallel Nicol or crossed Nicol arrangement with a liquid crystal cell 3 interposed on the rotating means 5 between them. Next, the optical axis of the phase plate 4 is set to coincide with the transmission axis of the polarizer 2. Then, the phase plate 4 is rotated by the controller 8 and the rotating means 5, and a rotation angle e at which the detection intensity of the photosensor 7 has an extreme value is measured. Then, the rotation angle α is substituted into Eq. (11), and the thickness of the birefringence layer (liquid crystal layer 3) is calculated with the computer 9. Thus, the thickness of the birefringence layer (liquid crystal layer 4) is calculated.

The present embodiment has several advantages. Because the thickness can be measured with a very simple optical system, a measurement apparatus can be provided at a low cost. Further, because the measurement can be performed at a high rate of speed, the number of samples taken can be increased from a time when a sample test is taken to a time when total inspection is completed. Thus, a yield in a fabrication process that uses this apparatus may be increased. Still further, because samples having a twist angle of liquid crystal other than 90° can be measured in contrast to prior art, various liquid crystals can be measured.

Though a simple phase plate 4 is used in the embodiment, a Babinet Soleil compensator having a combination of phase plates may also be used.

In the embodiment, a liquid crystal layer is an object to be measured. However, the object is not limited to liquid crystal, and the thickness of any object having birefringence can be measured.

Figure 11:
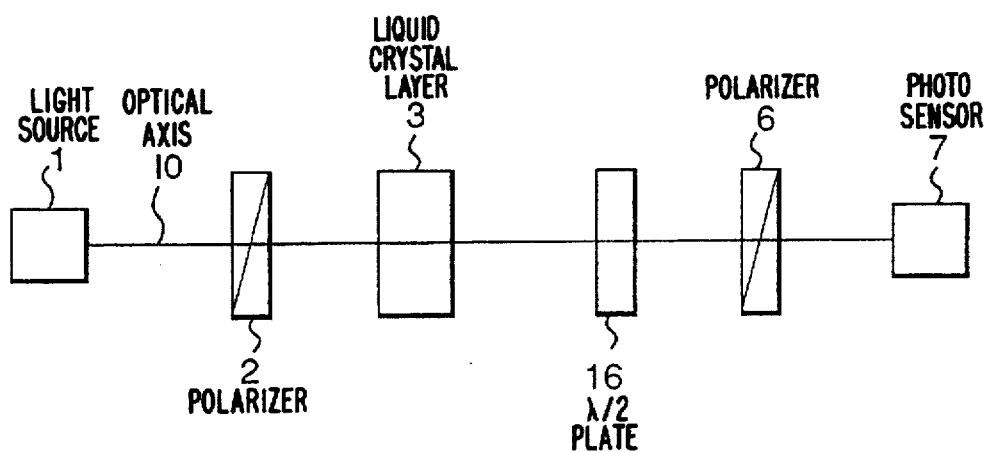
FIG. 11 is a diagram of another basic optical system for measuring a thickness of birefringence layer of a second embodiment of the invention.

Next, a second embodiment of the invention is explained for measuring the thickness of a birefringence layer. FIG. 11 shows a basic optical system of the second embodiment wherein like reference characters denote substantially the same components shown in FIG. 1.

Figure 12:
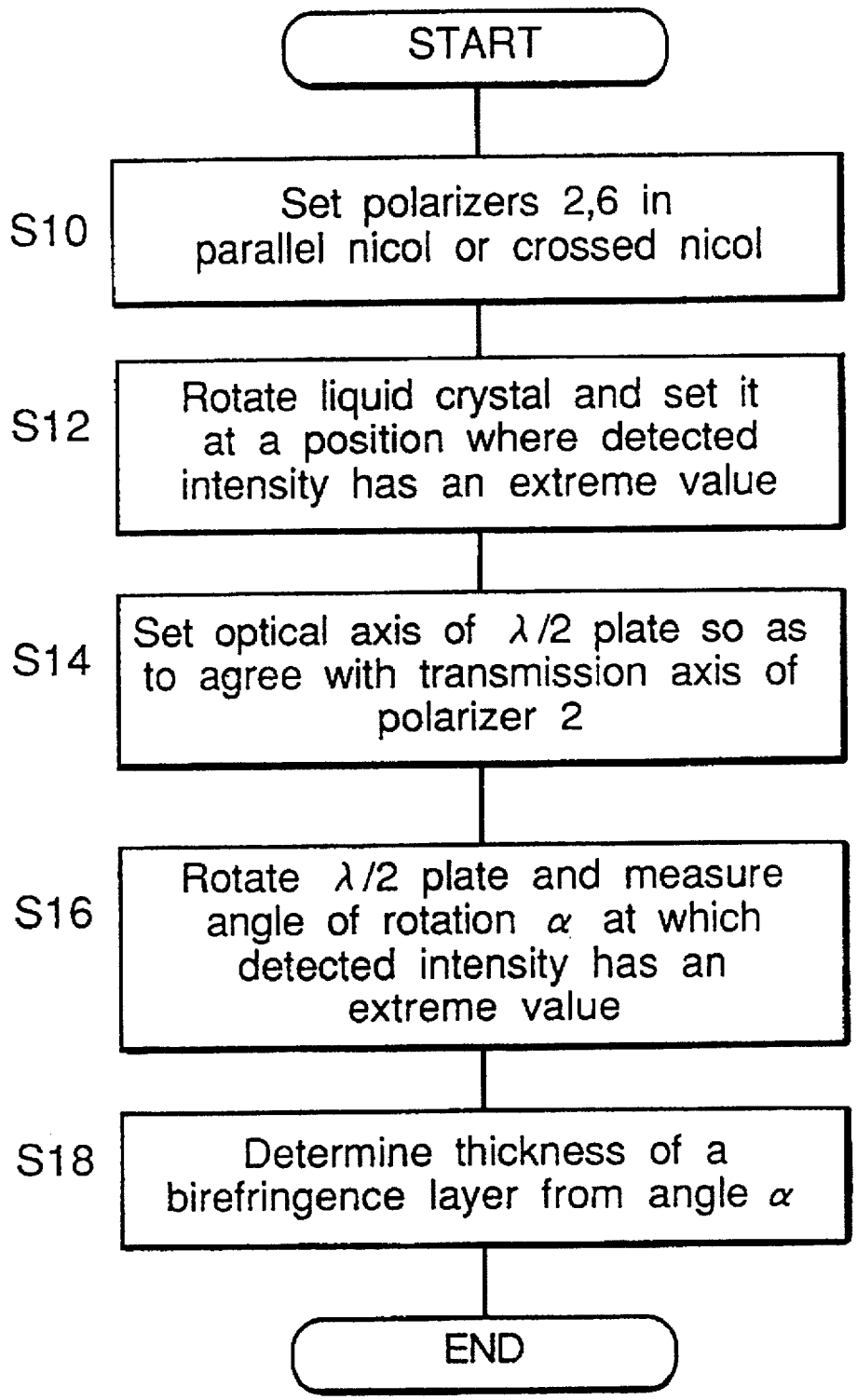
FIG. 12 is a flow chart of the measuring method of the second embodiment.

Next, with reference to the flowchart shown in FIG. 12, the measurement of a thickness of a birefringence layer such as a liquid crystal layer in the above-mentioned optical system is explained. First, the polarizers 2 and 6 are set in a parallel Nicol or crossed Nicol arrangement (step S10). Then, the liquid crystal 3 is rotated, and is set at a position where the detection intensity of the photosensor 7 has an extreme value (step S12). Next, the optical axis of the λ/2 plate (half-wave plate) 16 is set to coincide with the transmission axis of the polarizer 2 (step S14). Then, the λ/2 plate 16 is rotated, and a rotation angle α at which the detection intensity of the photosensor 7 has an extreme value is measured (step S16). Then, the rotation angle α is substituted into Eq. (18) explained later, and the thickness of the birefringence layer (liquid crystal layer) is calculated (step S18).

Next, the principle of the measuring method is explained with reference to numerical formulas, and it is shown that the thickness of a liquid crystal layer can be measured even if the rubbing direction φ of liquid crystal is not known.

When the λ/2 plate 16 is not used, the Jones vector $G(G_x, G_y)$ of a light transmitted through the polarizer 6 is written in Eq. (13), and an intensity H detected by the photosensor 7 is shown in Eq. (14).

$$G = \begin{pmatrix} G_x \\ G_y \end{pmatrix} = DBA. \quad (13)$$

$$H = |G_x|^2 + |G_y|^2. \quad (14)$$

Generality is not lost if the direction of the transmission axis $e_x$ of the polarizer 2 is taken as $e_y=0$, as in the first embodiment. Then, $e_z$ is set at zero. Then, the direction of the transmission axis $e_x$ of the other polarizer 6 is taken at 0° for a parallel Nicol arrangement or at 90° for a crossed Nicol arrangement.

In the case of a parallel Nicol arrangement, the intensity H1 detected by the photosensor 7 is shown in Eq. (15), and in the case of a crossed Nicol arrangement, the intensity H2 detected by the photosensor 7 is shown in Eq. (16).

$$H_1 = H_{e_y=0, e_z=0} \quad (15)$$

$$= p^2 + q^2$$

$$= \cos^2(\gamma)\cos^2(\theta) + \frac{\theta}{2\gamma}\sin(2\gamma)\sin(2\theta) +$$

$$\frac{\theta^2}{\gamma^2}\sin^2(\gamma)\sin^2(\theta) + \frac{\beta^2}{\gamma^2}\sin^2(\gamma)\cos^2(\theta + 2\phi).$$

$$H_2 = H_{e_y=0, e_z=\frac{\pi}{2}} \quad (16)$$

$$= r^2 + s^2$$

$$= \cos^2(\gamma)\sin^2(\theta) - \frac{\theta}{2\gamma}\sin(2\gamma)\sin(2\theta) +$$

$$\frac{\theta^2}{\gamma^2}\sin^2(\gamma)\cos^2(\theta) + \frac{\beta^2}{\gamma^2}\sin^2(\gamma)\sin^2(\theta + 2\phi).$$

As will be understood from Eqs. (15) and (16), the fourth terms in Eqs. (15) and (16) change as the liquid crystal layer 3 is rotated, and the detection intensity is changed.

The value at an extreme value of the detection intensity is determined as φ where partial differentials of Eqs. (15) and (16) with φ become zero, and it is shown in Eq. (17).

$$\phi = (m \times \pi - 2 \times \theta)/4, \quad (17)$$

wherein m is an integer.

By using Eq. (17), elements q and s of a Jones matrix of the liquid crystal layer relating to the rubbing direction φ of the liquid crystal cell has values shown in Table 3, and they are not relevant to the rubbing direction φ of the liquid crystal cell.

TABLE 3

| Polarization state | Extreme values | q | s |
|---|---|---|---|
| Parallel Nicol | Maximum | ±(β/γ)sin(γ) | 0 |
| Parallel Nicol | Minimum | 0 | ±(β/γ)sin(γ) |
| Crossed Nicol | Maximum | 0 | ±(β/γ)sin(γ) |
| Crossed Nicol | Minimum | ±(β/γ)sin(γ) | 0 |

When these values are substituted in Eq. (11), signs of ± are deleted in the first and second terms in the left hand side of the equation because they are terms of $q^2$, $s^2$ or qs. On the other hand, because a sign of ± remains in the third term of (ps+qr), the thickness of the liquid crystal layer cannot be determined uniquely. However, because the λ/2 plate 16 is used, sin δ=sin π=0 in the third term in Eq. (11). Thus, there exists no term which depends on the sign ±. Thus, the thickness of the liquid crystal layer can be determined uniquely.

By substituting π in the phase difference δ in Eq. (11) and by using Table 3, Eq. (18) is obtained.

$$\tan(4\alpha) = \frac{2pr}{r^2 + s^2 - p^2 - q^2} \quad (18)$$

If the difference between extraordinary and ordinary indices of the liquid crystal ($\Delta n = n_e - n_o$), twist angle of the liquid crystal ($\theta$), the measurement wavelength ($\lambda$) and the rotation angle $\alpha$ of the phase plate at an extreme value are known in Eq. (18), only the thickness d of the liquid crystal layer is not known. Then, the thickness d can be determined by solving Eq. (18).

Figure 13:
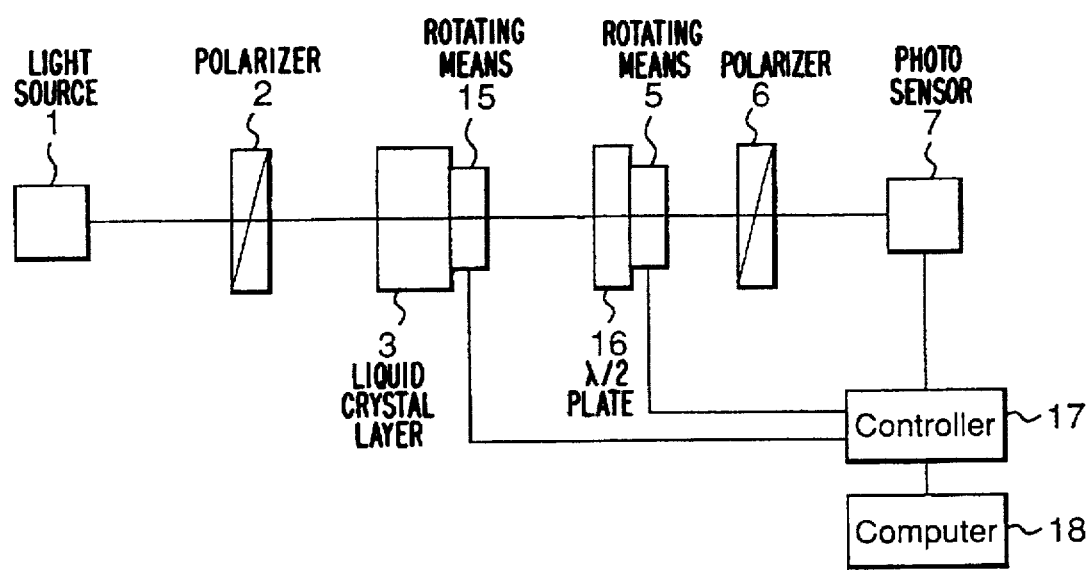
FIG. 13 is a diagram of another apparatus for measuring a thickness of birefringence layer.

FIG. 13 shows an apparatus for measuring a thickness of a birefringence layer wherein like reference numbers represent like components having the same function. A rotating means 15 rotates the liquid crystal layer 3. A controller 17 controls the rotation of the rotation means 15 for the liquid crystal layer 3 and the rotating means 5 for the phase plate 16. A computer 18 calculates the thickness d of the liquid crystal 3 as an object to be measured according to the rotation angle of the $\lambda/2$ plate 16 obtained with the controller 17.

A method of measuring the thickness of a birefringence layer in the optical system in the apparatus is explained with reference to the flowchart of FIG. 12. First, the polarizers 2 and 6 are set in a parallel Nicol or crossed Nicol arrangement. Next, the liquid crystal layer 3 is set on the rotating means 15 therefor, and it is rotated by the rotating means 15 which is controlled by the controller 17. Thus, the liquid crystal layer is set at a position at which the detection intensity of the photosensor 7 has an extreme value. Next, the optical axis of the $\lambda/2$ plate 16 is set to coincide with the transmission axis of the polarizer 2. Then, the $\lambda/2$ plate 16 is rotated by the rotating means 5 which is 17 controlled by the controlling means 17, and a rotation angle $\alpha$ at which the detection intensity of the photosensor 7 has an extreme value is measured. Then, the rotation angle $\alpha$ is substituted into Eq. (18) as explained above, and the thickness of the liquid crystal layer is calculated with the computer 18.

As described above, advantages similar to those in the first embodiment are realized. Further, by rotating the liquid crystal layer 3 to set it at an extreme value, the thickness of the liquid crystal layer (birefringence layer) is precisely determined according to the rotation angle of the $\lambda/2$ plate even if the rubbing direction of the liquid crystal is not known.

Although the present invention has been fully described in connection with the preferred embodiments thereof with reference to the accompanying drawings, it is to be noted that various changes and modifications are apparent to those skilled in the art. Such changes and modifications are to be understood as being included within the scope of the present invention as defined by the appended claims.

What is claimed is:

1. A method for measuring a thickness of a birefringence layer of an object, comprising:

providing the object having the birefringence layer in a light path of a light beam having a single wavelength, and between first and second polarizers which are arranged in a parallel nicol or crossed nicol manner;

providing a phase plate between the first and second polarizers such that a transmission axis of the first polarizer coincides with an optical axis of the light path;

rotating the phase plate and measuring a rotational angle of the phase plate for an angle at which an optical intensity of light transmitted from the second polarizer has a maximum value; and calculating the thickness of the birefringence layer according to the measured rotational angle of the phase plate.

2. The method according to claim 1, wherein the phase plate comprises a Babinet-Soleil compensator.

3. The method according to claim 1, wherein the birefringence layer comprises a liquid crystal layer.

4. An apparatus for measuring a thickness of a birefringence layer of an object, comprising:

a light source which emits an optical light beam having a single wavelength along a light path;

first and second polarizers arranged in the optical light path and which are arranged in a parallel nicol or crossed nicol manner;

a phase plate interposed between said first and second polarizers such that a transmission axis of said first polarizer coincides with an optical axis of the light path;

a phase plate rotator operatively coupled to said phase plate;

a photosensor which detects light transmitted from said second polarizer;

a controller which makes said phase plate rotator rotate said phase plate to a rotation angle at which an optical intensity of the light transmitted from said second polarizer has a maximum value; and a computer which calculates the thickness of the birefringence layer according to the rotation angle.

5. The apparatus according to claim 4, wherein said phase plate comprises a Babinet-Soleil compensator.

6. The apparatus according to claim 4, wherein the birefringence layer comprises a liquid crystal layer.

7. A method for measuring a thickness of a birefringence layer of an object which has an orientation direction at an incident side, comprising:

providing the object having a birefringence layer in a light path of a light beam having a single wavelength, and between first and second polarizers which are arranged in a parallel nicol or crossed nicol manner;

rotating the object and setting the birefringence layer such that an optical intensity of light transmitted from the second polarizer has a maximum value;

providing a $\lambda/2$ plate located between the first and second polarizers such that a transmission axis of the first polarizer coincides with an optical axis of the light path;

rotating the $\lambda/2$ plate and measuring a rotational angle of the phase plate for an angle at which an optical intensity of light transmitted from the second polarizer has a maximum value; and calculating a thickness of the birefringence layer according to the measured rotational angle of the $\lambda/2$ plate.

8. The method according to claim 7, wherein the birefringence layer comprises a liquid crystal layer.

9. An apparatus for measuring a thickness of a birefringence layer of an object, comprising:

a light source which emits an optical light beam having a single wavelength along a light path;

first and second polarizers arranged in the optical light path and which are arranged in a parallel nicol or crossed nicol manner;

an object rotator operatively coupled to the object;

a λ/2 plate interposed between said first and second polarizers such that a transmission axis of said first polarizer coincides with an optical axis of the light path;

a λ/2 plate rotator operatively coupled to said λ/2 plate;

a photosensor which detects light transmitted from said second polarizer;

a controller which makes said object rotator rotate the object to a particular position and makes said λ/2 plate rotator rotate said λ/2 plate to a particular rotational angle, wherein the particular position and particular rotational angle respectively occur when the optical intensity of the light transmitted from said second polarizer has a maximum value; and a computer which calculates the thickness of the birefringence layer according to the rotation angle.

10. The method according to claim 9, wherein the birefringence layer comprises a liquid crystal layer.

* * * * *